United States Patent [19]

Bafford et al.

[11] 4,204,075

[45] May 20, 1980

[54] PROCESS FOR DI-ORGANIC PEROXIDES

[75] Inventors: Richard A. Bafford, Tonawanda; Orville L. Mageli, Kenmore, both of N.Y.

[73] Assignee: Pennwalt Corporation, Philadelphia, Pa.

[21] Appl. No.: 938,192

[22] Filed: Aug. 30, 1978

Related U.S. Application Data

[62] Division of Ser. No. 771,334, Oct. 28, 1968, Pat. No. 4,061,317.

[51] Int. Cl.$^2$ ............................................. C07C 179/06
[52] U.S. Cl. ........................................ 568/562; 568/561
[58] Field of Search ..................... 568/562, 561, 576

[56] References Cited

U.S. PATENT DOCUMENTS

| | | | |
|---|---|---|---|
| 3,267,066 | 8/1966 | Tijssen ................................. | 568/558 |
| 3,310,588 | 3/1967 | Kloosterman et al. .............. | 568/578 |
| 3,337,639 | 8/1967 | Stedhouder et al. ................ | 568/563 |

*Primary Examiner*—Werren B. Lone

[57] ABSTRACT

An aliphatic or cycloaliphatic hydroperoxide, an olefin such as a 1-aromatic-1-substituted ethylene and a halide corresponding to the ethylene are reacted under essentially anhydrous conditions, in the absence of a free acid, at a temperature below the decomposition temperature of the halide to obtain a peroxide corresponding to the hydroperoxide and the ethylene.

Preferably the product peroxide is recovered by treating the reaction product mixture with aqueous alkali metal hydroxide to destroy the halide and hydroperoxide therein; then distilling the treated mixture in the presence of a substantial amount of liquid water at subatmospheric pressure to remove overhead impurities.

Example: Dicumyl peroxide is prepared by reacting at about 30° C. for about 5 hours cumene hydroperoxide, α-methylstyrene and cumyl chloride, which compounds has been charged to the reaction zone in a mole ratio of 1.25:0.86:0.14 and treating the reaction product mixture with aqueous alkali metal hydroxide to remove cumyl chloride and cumene hydroperoxide to obtain a product mixture including dicumyl peroxide; and adding 2-10 parts of liquid water to the product mixture in a distillation zone and vaporizing water and impurities at a temperature of about 30°-80° C. at a pressure of about 0.01-0.5 atmospheres and continuing said vaporization until essentially no oily liquid is obtained in a condensor receiving vapors from said zone, under conditions such that a substantial amount of liquid water is present in said zone in contact with peroxide product.

4 Claims, No Drawings

PROCESS FOR DI-ORGANIC PEROXIDES

This is a division of application Ser. No. 771,334 filed Oct. 28, 1968, now U.S. Pat. No. 4,061,317.

BACKGROUND OF THE DISCLOSURE

1. Field of the Invention

This invention relates to organic peroxides, such as dicumyl peroxide. More particularly, the invention relates to the preparation of such organic peroxides and also to the purification thereof.

2. Description of the Prior Art

Extensive prior art exists on the preparation of aralkyl and alkyl peroxides. The prior art can best be summarized under three major methods of preparation.

1. The acid-catalyzed condensation of a hydroperoxide with an alcohol [Milas and Harris, JACS, 60, 2434 (1938); Milas and Surgenor, JACS, 68, 205 (1946); Milas and Perry, JACS, 68, 1938 (1946); U.S. Pat. Nos. 2,668,180 (1954), 3,254,130 (1966), 3,310,588 (1967); and 3,337,639 (1967).] This is probably the most widely known and widely used method for the preparation of alkyl peroxides. This method is best used where the product peroxide is not acid-sensitive, where the hydroperoxide is relatively stable to acid, and where the alcohol is tertiary and readily forms a carbonium ion. This method is less satisfactory when one or more of the above conditions are not met. For example, the acid-sensitivity of cumene hydroperoxide is widely known. Cumyl t-butyl peroxide can be prepared in good yield by the sulfuric acid catalyzed condensation of cumyl alcohol and t-butyl hydroperoxide but can not be prepared by the sulfuric acid catalyzed condensation of cumene hydroperoxide and t-butyl alcohol. Peroxides containing an aralkyl group are also somewhat acid-sensitive although to a much less degree than cumene hydroperoxide. Thus, dicumyl peroxide and cumyl t-butyl peroxide will decompose in the presence of mineral acids even at room temperature giving among other things phenol and acetone. Several patents (see list above) teach the preparation of dicumyl peroxide by the acid-catalyzed condensation of cumene hydroperoxide and cumyl alcohol; we have found such processes to be unsatisfactory and very hazardous.

2. The acid-catalyzed addition of a hydroperoxide to an olefin [Milas and Harris; Milas and Surgenor; Davies et al., J. Chem. Soc., 2200 (1954) and U.S. Pat. No. 3,267,066 (1967)].

This process has the same advantages and disadvantages of (1) above. It is generally used with olefins which readily form tertiary carbonium ions such as the acid-catalyzed addition of t-butyl hydroperoxide to isobutylene or diisobutylene. It is less satisfactory for olefins like α-methylstyrene which readily undergo acid-catalyzed telomerization. U.S. Pat. No. 3,267,066 shows the preparation of dicumyl peroxide from α-methylstyrene, cumene hydroperoxide and hydrogen chloride.

3. The displacement reaction between an alkali metal salt of a hydroperoxide and an alkyl halide [U.S. Pat. No. 2,403,709 (1946), T. W. Campbell and G. M. Coppinger, J. Am. Chem. Soc., 73 1789 (1951), and U.S. Pat. No. 3,247,259 (1966).] This is an especially good method for the preparation of peroxides from primary or secondary halides or sulfates but is of dubious value for tertiary halides since dehydrohalogenation is far more rapid than the displacement reaction.

4. There are several processes for the preparation of specific peroxides. Dicumyl peroxide is formed as a minor byproduct of the autoxidation of cumene to cumene hydroperoxide. It is not a practical process for the preparation of dicumyl peroxide but represents a byproduct of large scale producers of phenol from cumene.

Another method of preparation of aralkyl peroxides is the copper ion-catalyzed decomposition of hydroperoxides in the presence of substrates. Thus cumyl t-butyl peroxide (60% yield) can be prepared by heating at 67° for 18 hours a mixture of cumene, t-butyl hydroperoxide and cuprous chloride. However, the stoichiometry requires the consumption of two moles of hydroperoxide for each mole of peroxide produced. Thus only 30% of the hydroperoxide is converted to peroxide in this reaction.

PURIFICATION

At this time the art utilizes two methods for the purification of aralkyl peroxides, namely, low temperature crystallization or vacuum distillation; U.S. Pat. Nos. 2,668,180; 3,254,130; 3,310,588; 3,267,066; and 2,691,683 (1954).

Crude dicumyl peroxide is purified by cooling the reaction mixture to $-10°$ C. and allowing crystallization to occur. However, this gives an oily solid which then must be recrystallized from a suitable solvent such as methanol. In addition, unless the crude mixture contains at least 75% dicumyl peroxide, crystallization will not take place. Thus high assay cumene hydroperoxide is needed as starting material.

The other method for purifying dicumyl peroxide consists of distilling impurities by heating the crude peroxide at 90°–110° under high vacuum for several hours. The hazards of heating peroxides at these temperatures and the necessity of a high vacuum make this process commercially unattractive. This distillation can give a product assaying about 90% but it has a dark amber color and must be decolorized and recrystallized to be acceptable commercially; also these products may go off color in ordinary storage.

OBJECTS

The main object of the invention is a process for the preparation of certain peroxides, especially acid-sensitive peroxides, by a procedure that does not use a free-acid catalyst.

Another object of the invention is a purification procedure for certain peroxides which produces colorless product by a vaporization operation that does not require excessively high temperatures.

Other objects will become apparent in the course of the detailed description of the invention.

SUMMARY OF THE INVENTION

A. The peroxide preparation process of the invention comprises:

(1) reacting a hereinafter defined olefin, a reactive organic halide, and organic hydroperoxide, in the absence of a free acid, under essentially anhydrous conditions, at a temperature below the temperature at which substantial decomposition of said organic halide occurs, where (2) said olefin has the general formula

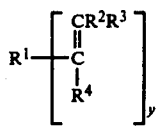

where
(a) y is an integer equal to 1, 2 or 3;
(b) $R^1$ is an aromatic radical;
(c) $R^2$ and $R^3$ are each H, aliphatic, cycloaliphatic, or aromatic radicals;
(d) $R^4$ is an aliphatic or aromatic radical;
(e) =$CR^2R^3$ may be a cyclic group;
(f)

may be a cyclic group;
(g)

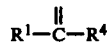

may be a fused ring group;
(h)

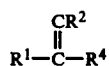

may be a fused ring group having the C=C portion as a part of the fused ring; and
(i) when $R^1$ is substituted on more than one ring carbon atom, only one ring carbon atom ortho to a

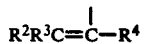

group may be joined to a substituent group;
(3) said reactive organic halide has the general formula

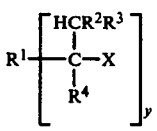

where X is I, Br, Cl, or F; and
(4) said organic hydroperoxide has the general formula

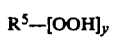

where $R^5$ is an aliphatic or cycloaliphatic radical.

B. The preferred preparation process of the invention comprises:
(1) reacting a hereinafter defined olefin, a reactive organic halide, and organic hydroperoxide, in the absence of a free acid, under essentially anhydrous conditions, where
(2) said olefin has the general formula

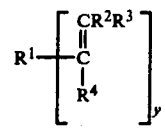

where
(a) y is an integer equal to 1, 2, or 3;
(b) $R^1$ is phenyl, a fused benzene ring group having 2-3 rings, or a doubled benzene ring group;
(c) $R^2$ and $R^3$ are each H, alkyl, cycloalkyl, phenyl, or a corresponding halo substituted radical;
(d) $R^4$ is alkyl, cycloalkyl, phenyl, or a corresponding halo substituted radical; and
(e) =$CR^2R^3$ may be a cyclic group;
(f)

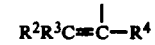

may be a cyclic group;
(g)

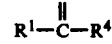

may be a fused ring group;
(h)

may be a fused ring group having the C=C portion as a part of the fused ring; and
(i) when $R^1$ is substituted on more than one ring carbon atom, only one ring carbon atom ortho to a

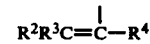

group may be joined to a substituent group;
(3) said reactive organic halide has the general formula

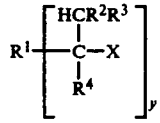

where X is Br or Cl;
(4) said organic hydroperoxide has the general formula

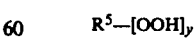

where $R^5$ is an aliphatic hydrocarbon radical, a cycloaliphatic hydrocarbon radical, or the corresponding halo substituted radical;
(5) at a temperature in the range of about 0°–60° C. for a time in the range of about 1–12 hours with the longer times being associated with the lower temperatures;

(6) the mole ratio of —OOH groups in said hydroperoxide charged to the ethylenic bonds in said olefin charged is about 2.0-1.1:1; and (7) said halide is charged in an amount of about 10-20 moles percent based on olefin charged.

C. The purification process of the invention is directed to impure organic peroxides having the general formula

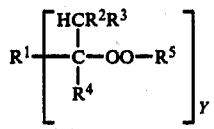

said impure peroxide being essentially free of acidic materials and said impurities having an appreciable lower boiling point than said peroxide where said impure peroxide is charged along with 2-10 parts by weight of liquid water, based on said impure peroxide, to a distillation zone; vaporizing water and impurities at a temperature of about 30°-80° C. at a pressure of about 0.01-0.5 atmospheres and continuing said vaporization until essentially no oily liquid is obtained in a condensor receiving vapors from said zone, under conditions such that a substantial amount of liquid water is present in said zone in contact with peroxide product, wherein (a) Y is an integer equal to 1, 2, or 3;
(b) $R^1$ is an aromatic radical;
(c) $R^2$ and $R^3$ are each H, aliphatic, cycloaliphatic, or aromatic radicals;
(d) $R^4$ is an aliphatic or aromatic radical;
(e)

may be a cyclic group;
(f)

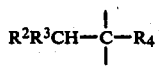

may be a cyclic group;
(g)

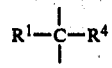

may be a fused ring group; and
(h) $R^5$ is an aliphatic or cycloaliphatic radical.

The purification process is preferred to be used with the product mixture from the preparation process of the invention, which mixture has been treated with aqueous alkali metal hydroxide to remove organic halide and unreacted hydroperoxide.

DESCRIPTION OF THE INVENTION AND EXAMPLES

The peroxide preparation process of the invention requires as necessary components of the feed a particular class of olefins, a particular class of organic halides, and a particular class of organic hydroperoxides. The components of the feed may be charged to the reaction zone in any order or may be premixed.

In this process there is no initial rapid reaction or heat build-up. There is no need to moderate the reaction with a solvent or to control the reaction rate by slow addition of one of the materials.

In the case of a batch reactor, it is preferred to charge the entire feed to the reactor before the start of the reaction. In the case of a continuous reaction system, it is preferred to charge the components simultaneously, for example by premixing, to the reaction zone in the desired proportions.

The reaction may be carried out in the presence of an inert organic solvent for one or more of the feed components. However, usually the reaction is carried out without using any added solvent.

The reaction is carried out without the use of any added free-acid such as is conventionally used in the reaction of olefin and hydroperoxide.

The reaction can best be accomplished by having essentially anhydrous conditions in the reaction zone.

It has been observed that the temperature at which substantial decomposition of the organic halide occurs is the controlling maximum temperature for the preparation reaction. In general the reaction can be carried out over the range of temperatures of about 0° (zero-)-60° C. When operating with the preferred olefins, halides, and hydroperoxides, it is preferred to carry out the reaction at a temperature in the range of about 20°-50° C.

It has been observed that the yield of peroxide product is influenced by both the temperature at which the reaction is carried out and the time for which the reaction is permitted to continue. The proportions of the three components of the feed also has an influence on the yield of peroxide product. In general, the higher the temperature used, the shorter the times that should be used when attempting to maximize yield—at a given proportion in the feed.

It is to be understood that each feed, not only in terms of proportions but the components which make up the feed, appears to have its own temperature-time relation for the optimum yield of peroxide product. However, in general, the reaction time is in the range of about 1 hour to about 12 hours, with the shorter times being desirably associated with the higher temperatures. At the preferred temperature range of about 20°-50° C., the desirable time range is about 2-10 hours.

It has been observed that each combination of feed has a temperature and time relation which at first causes the yield of peroxide product to increase and then causes the yield to decrease. For a given feed, at a fixed time, the yield reaches a maximum at some temperature; raising the temperature beyond this level results in a yield decrease. For a given feed, at a fixed temperature the yield reaches a maximum at some point in time; lengthening the time beyond this point results in a yield decrease.

It is thought that this yield behavior cannot be explained merely by thermal or chemical decomposition of the organic halide, and/or the hydroperoxide, and/or the peroxide product. Examination of the data indicates that a complicated combination of factors must be influencing the course of the reaction.

It is believed that these statements about the influence of feed components, proportions thereof, and temperature and time when taken with the numerous examples, especially the series of runs in Examples 7, 8, and 9, will enable anyone to readily determine for a given feed the optimum yield conditions.

It is pointed out that the economics of raw materials and process costs may dictate a different optimum yield than that obtainable when these economic factors are ignored.

In the overall view, the reaction involves the addition of the —OOH group from the hydroperoxide to the ethylenic bond of the olefin to form a bridge between the erstwhile olefin and the erstwhile hydroperoxide. Therefore the proportion of olefin to hydroperoxide in the feed must be related to the reactive portion of the olefin and hydroperoxide respectively. In general the feed contains the organic hydroperoxide and the olefin in a mole ratio of —OOH groups contained in the hydroperoxide to reactive ethylenic bonds contained in the olefin on the order of about 5:1 to 0.5:1 or, in other words, 5–0.5:1.

It has been discovered that when other conditions are fixed, the yield of peroxide product is increased as the amount of hydroperoxide present in the feed is increased. It is definitely beneficial to operate with an excess of hydroperoxide over the theoretical amount needed to react with the reactive ethylenic bonds. The preferred mole ratio of —OOH groups charged to reactive ethylenic bonds charged is about 2.0–1.1:1.

To illustrate: The reaction of cumene hydroperoxide and α-methylstyrene requires theoretically one mole of each component; a ratio of 1:1. The reaction of t-butyl hydroperoxide and of bis(isopropenyl)benzene requires two moles of the hydroperoxide for each mole of the bis compound; a mole ratio of 1:1 in terms of —OOH and C=C present.

The presence of the reactive organic halide is essential to the carrying out of the overall reaction between the olefin and the hydroperoxide. Test 10 demonstrates the critical importance of this component. In general, the feed contains an amount of the halide of about 2–20 mole percent based on the amount of olefin charged. Excessive halide present appears to have an adverse effect on the yield. When operating with the preferred proportion of hydroperoxide and olefin, it is preferred to use about 10–20 mole percent of halide based on the amount of olefin charged.

It has been observed that with the feed: cumene hydroperoxide, α-methylstyrene, and cumyl chloride the best results at any combination of temperature and time appear to be obtained with a mole ratio of the three components, in the above order respectively, of about 1.25:1.0:0.15.

THE ORGANIC HYDROPEROXIDES

The organic hydroperoxide charged to the preparation process of the invention has the general formula:

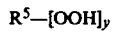

$R^5$—[OOH]$_y$

Preferably $R^5$ is an aliphatic hydrocarbon radical, a cycloaliphatic hydrocarbon radical, or a corresponding halo substituted radical, i.e., halo-aliphatic hydrocarbon radical or halo-cycloaliphatic hydrocarbon radical. The term "aliphatic" includes the aromatic substituted open chain hydrocarbon radicals, for example, benzyl and cumyl. The term "cycloaliphatic" includes the aromatic substituted closed chain hydrocarbon radical, such as, phenylcyclohexyl.

Especially preferred $R^5$ is lower alkyl, lower alkenyl, lower alkynyl, cycloalkyl, cycloalkenyl, cycloalkyl-lower alkyl, aralkyl, aralkenyl, the corresponding di- and tri-valent radicals, or the corresponding halo substituted radicals.

Of most interest is the hydroperoxide wherein one peroxy oxygen of —OOH is joined to a tertiary carbon atom of $R^5$. This is shown by the formula.

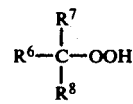

where:

$R^7$ and $R^8$ are each lower alkyl or cycloalkyl. $R^7$—C—$R^8$ may be a carbocyclic ring or a heterocyclic ring containing oxygen as part of the ring. $R^6$ is lower alkyl, lower alkenyl, lower alkynyl, cycloalkyl, cycloalkylalkyl, aryl, aryloxy, alkoxy, hydroxyalkyl, or one of the following radicals shown by structure

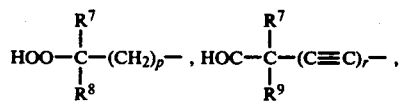

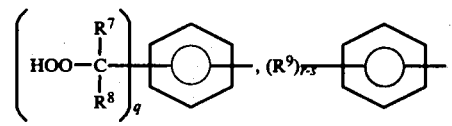

$R^{9\,L}$ is lower alkyl, cycloalkyl, aryl, aryloxy, alkoxy, halo or nitro.

p is an integer from 1 to 10.

q is an interger 1 or 2.

r and s are integers from 1 to 5.

Hydroperoxides are illustrated by alkyl hydroperoxides, such as t-butyl hydroperoxide, t-amyl hydroperoxide, 1,1,3,3 tetramethylbutyl hydroperoxide, 2,5-dimethyl-2,5-dihydroperoxyhexane and 2,7-dimethyl-2,7-dihydroperoxyoctane; aralkyl hydroperoxides such as cumene hydroperoxide, cymene hydroperoxide, diisopropylbenzene monohydroperoxide, diisopropylbenzene dihydroperoxide, 3,5-Bis(α-hydroperoxyisopropyl) cumene and 1,3,5 triisopropylbenzene trihydroperoxide; cycloalkyl hydroperoxides such as decalin hydroperoxide, pinane hydroperoxide, p-menthane hydroperoxide, 1-methylcyclohexyl hydroperoxide and 1-methylcyclopentyl hydroperoxide; acetylenic hydroperoxides such as 2-methyl-2-hydroperoxybutyne-3, 1-hydroperoxycyclohexylacetylene, 2,5-dimethyl-2,5-dihydroperoxyhexyne-3 and 3-methyl-3-hydroperoxypentyne-1 and other peroxides such as 2-methyl-2-hydroperoxytetrahydrofuran, 1-methoxy-1-hydroperoxycyclohexane, 2-isoamyloxy-2-hydroperoxypropane, 2-methyl-2-hydroperoxytetrahydropyran and 2-hydroperoxytetrahydropyran; hydroxy alkyl by 2,5-methyl-2-hydroxy-5-hydroperoxy hexane. Actually the scope of operable hydroperoxides is broad; acid-sensitive, base-sensitive and normal hydroperoxides can be used in this process since it is carried out under anhydrous "neutral" conditions.

THE OLEFIN

The olefin charged to the preparation process has the formula:

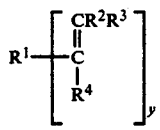

Preferably R¹ is phenyl, a fused benzene ring group having 2-3 rings, or a doubled benzene ring group; R² and R³ are each H, alkyl, cycloalkyl, phenyl, or a corresponding halo substituted radical; and R⁴ is alkyl, cycloalkyl, phenyl, or a corresponding halo substituted radical The phenyl and naphthalene radical monoolefins are illustrated by the formulas:

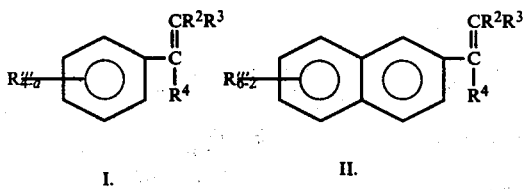

I.                II.

It is evident that these monoolefins can be considered as derivatives of ethylene, specifically 1-aromatic-1-substituted ethylenes.

In Formulas I and II there are two ring carbon atoms ortho to the ethylenic group. It has been observed that when both of these positions are substituted, even though one be an ethylenic group, the reaction rate is hindered to such an extent that these compounds must be considered ineffective. In the olefins used in the process of the invention only one ring carbon atom ortho to an ethylenic group may be joined to a substituent group.

In Formulas I and II the maximum number of R''' groups is 4 and 6 respectively. The minimum number is zero (0). Therefore, n is an integer equal to 0-4; and m is an integer equal to 0-6.

When n is 3, R''' may be joined to either R³ or R⁴ to form a fused ring styrene.

R''' is a substituent radical which does not interfere with the peroxide formation reaction, such as, lower alkyl, cycloalkyl, aryl, alkoxy, aryloxy, halo, nitro, and the corresponding halo substituted radicals.

Illustrative olefins coming within Formulas I and II and also some olefins having two and three ethylenic groups are set out in Table 1.

TABLE 1

| R² | R³ | R⁴ | R''' | n | Name |
|---|---|---|---|---|---|
| | | | Structure I | | |
| H | H | CH₃ | — | 4 | α-Methylstyrene |
| H | C₂H₅ | CH₃ | — | 4 | 2-Phenylbutene-2 |
| H | H | C(CH₃)₃ | — | 4 | α-t-Butylstyrene |
| H | H | C₆H₅ | — | 4 | 1,1 Diphenylethylene |
| CH₃ | CH₃ | CH₃ | — | 4 | 2-Phenyl-3-methylbutene-2 |
| H | H | CH₃ | CH₃ | 3 | p,α-Dimethylstyrene |
| H | H | CH₃ | CH(CH₃)₂ | 3 | p-Isopropenylcumene |
| H | H | CH₃ | C(CH₃)₃ | 3 | p-t-Butyl-α-methylstyrene |
| H | H | CH₃ | C₆H₅ | 3 | 4-Isopropenylbiphenyl |
| H | H | CH₃ | Cl | 3 | p-Chloro-α-methylstyrene |
| H | H | CH₃ | Cl | 3 | m-Chloro-α-methylstyrene |
| H | H | CH₃ | F | 3 | p-Fluoro-α-methylstyrene |
| H | H | CH₃ | Cl | 2 | 3,4 Dichloro-α-methylstyrene |
| H | H | CH₃ | Br | 3 | p-Bromo-α-methylstyrene |
| H | —(CH₂)₄— | | — | 4 | 1-Phenylcylcyclohexene-1 |
| CH₃ | —(CH₂)₄— | | — | 4 | 1-Phenyl-2-methylcyclohexene-1 |
| H | —(CH₂)₃— | | — | 4 | 1-Phenylcyclopentene-1 |
| H | H | CH₃ | —C(=CH₂)CH₃ | 3 | p-Diisopropenylbenzene |
| H | H | CH₃ | —C(=CH₂)CH₃ | 2 | 1,3,5 Triisopropenylbenzene |
| H | H | CH₃ | —C(=CH₂)CH₃ | 2 | 1,2,4 Triisopropenylbenzene |
| H | H | | —(CH₂)₃— | 3 | 1-Methylenetetralin |
| H | | CH₃ | CH₂— | | 1-Methylindene |
| H | H | CH₃ | —C(CH₃)₂—O—C(CH₃)₂— | | 4-Isopropenyl-α,α,α',α' tetramethylphthalan |
| H | H | CH₃ | —C(=CH₂)CH₃—C₆H₄— | 3 | p,p'-Diisopropenylbiphenyl |

TABLE 1-continued

| R² | R³ | R⁴ | R‴ | n | Name |
|---|---|---|---|---|---|
| H | H | CH₃ | 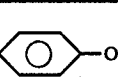 | 3 | p,p'-Diisopropenyl-diphenyl ether |
| H | H | CH₃ | 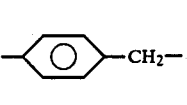 | 3 | p,p'-Diisopropenyl-diphenyl methane |
|   |   |    | Structure II |   |   |
| H | H | CH₃ | — | 6 | 1-Isopropenyl-naphthalene |
| H | H | CH₃ | — | 6 | 2-Isopropenyl-naphthalene |

Aralkenes of Formulas I and II can be prepared by the dehydration of the corresponding tertiary alcohols or by the vapor phase dehydrogenation of the hydrocarbons. For example, α-methylstyrene and p,α-dimethylstyrene are synthesized commercially by the dehydrogenation of cumene and cymene, respectively. The tertiary alcohols are prepared by conventional organic synthesis techniques such as the Grignard reaction or the chromic acid oxidation of hydrocarbons. Olefins of interest are the α-methylstyrene and di- and tri(isopropenyl)benzenes.

REACTIVE ORGANIC HALIDE

The reactive organic halide charged to the process of the invention has the formula:

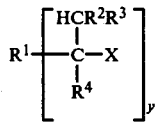

It is evident that the halides correspond to the defined olefin to which the elements of HX have been added. It is desirable that the halide added to the process, as part of the feed, have the same composition as the halide that would be obtained by adding HX to the olefin which is charged as part of the feed.

X is any halogen, i.e., I, Br, Cl, or F. It is preferred to use the bromo or chloro halides.

One or more methods of preparing halides coming within the definition are known to the art. Anyone of the olefins listed in Table 1 can be converted directly or indirectly to a halide suitable for use in the process of the invention.

DEFINITIONS

In the formulas aliphatic and cycloaliphatic are used in their broadest technical meaning; however, it is to be understood that substituents which may be present in the aliphatic or cycloaliphatic radical must be inert, i.e., do not interfere with the preparation reaction. Commonly the aliphatic radical will have 1-36 carbon atoms, usually 1-22, and the cycloaliphatic radical will have 3-12 ring carbon atoms, usually 4-8, in a single ring compound and 5-24 ring carbon atoms, usually 5-12, in a doubled or fused ring radical. It is to be understood that both aliphatic and cycloaliphatic may be substituted with one or more aromatic groups.

Aromatic is used in its broadest technical meaning and includes a single benzenoid ring, doubled (and higher) rings, and fused rings. These may be substituted with groups which are inert in the process or by one or more non-aromatic rings, including fused rings. Commonly these are phenyl, naphthyl and biphenyl radicals.

The above definitions are broad and intentionally so because the radical definitions do not affect the general utility of the compounds in the preparation of the process set forth herein.

A tertiary aliphatic radical is one where the free valence is associated with a carbon atom which is joined directly through its other valences with three other carbon atoms, for example, a t-butyl radical.

Lower alkyl is intended to have about 1-12 carbon atoms and usually 1-8 carbon atoms.

Alkyl, Alkenyl, and Alkynyl: Each group may include 1, 2, or more carbon atoms. Desirably each has 1-22 or 2-22 carbon atoms. Preferably each has 1-12 or 2-12 carbon atoms.

It is to be understood that the definitions above apply to all the R's herein before given for the hydroperoxide, olefin and halide to be used in the preparation process of the invention.

THE PURIFICATION PROCESS

The peroxide purification process of the invention is directed to an impure peroxide of the structure

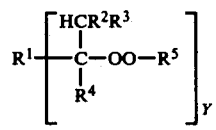

The process is especially directed to impure peroxides which have been prepared by the preferred preparation process.

The impure peroxide feed to the purification process must be essentially free of acidic materials and the impurities must have an appreciable lower boiling point than the peroxide.

The purification process is described as water vaporization-distillation operation because the impure peroxide is subjected to distillation conditions in the presence of liquid water, i.e., liquid water is present in the distillation zone along with the peroxide throughout the distillative purification.

In the purification process about 2-10 parts by weight of liquid water, based on the impure peroxide charge, more usually 3-10 parts, are charged to the distillation zone along with the impure peroxide. The distillation is carried out under conditions such that a substantial amount of liquid water is always present therein in contact with the peroxide; even at the completion of the distillation operation.

The water vaporization-distillation is carried out at sub-atmospheric pressure; one which permits distillation of the impurities at a temperature well below the thermal decomposition temperature of the peroxide. In general, this pressure is in the range of about 0.01–0.5 atmospheres and commonly with the preferred peroxides from the preparation process, the pressure is in the range of about 0.1–0.35 atmospheres.

The temperature in the distillation zone is maintained below about 80° C.; usually in the range of about 30°–80° C. Preferably the temperature is held between about 30°–60° C.

The distillation is continued until no "oily" liquid is obtained in a condensate from a condensor which receives vapors from the distillation zone.

When the charge to the vaporization-distillation process is peroxide made by the preparation process, it is necessary to first remove the halide and the unreacted hydroperoxide present in the peroxide product mixture from the preparation reaction. This is conventionally accomplished by agitating the peroxide reaction product mixture with aqueous alkali metal hydroxide. (This treatment demonstrates that the halide is present because of the slowness of the reaction of the hydroxide. This treatment converts the halide to the corresponding olefin.)

The hydroxide treated peroxide mixture may be washed with aqueous salt solution or with ordinary water, before being charged to the vaporization-distillation process.

At the end of the vaporization-distillation, the distillation bottoms consist essentially of high purity peroxide and liquid water. For normally solid peroxides, the bottoms are cooled, with agitation, and the peroxide rapidly crystallizes out. The solid may be recovered by filtration or centrifuging, and then air-dried. For normally liquid peroxides, the peroxide phase is decanted or centrifuged away from the aqueous phase. If necessary the liquid peroxide is dried with a suitable solid desiccant, such as sodium or magnesium sulfate.

For solid peroxides, the process gives a product typically having an assay in excess of 95%. For liquid peroxides, the process gives a product typically having an assay in excess of 90%.

The purification process is especially useful with dicumyl peroxide and t-butyl cumyl peroxide prepared by the preparation process because of the ease with which the high purity peroxide is recovered as a solid from the distillation bottoms.

EXAMPLES

Numerous examples of the preparation process and purification process are hereinafter set forth. (Test 10 is directed to an attempt to make peroxide directly from hydroperoxide and halide in the absence of olefin.) It is to be understood that these examples are not limiting with respect to the scope of the invention.

In the Examples, all yields of peroxide, except where stated otherwise, have been corrected on the basis of the assay of peroxide product.

In the Examples, the yields recorded have been calculated on the basis of the limiting reactant. However, where the hydroperoxide was not the limiting reactant, the yields were calculated on the basis that all of the olefin plus all of the halide could react to give peroxide.

For illustration: In the case of the feed, cumeme hydroperoxide (1.25 moles), α-methylstyrene (0.86 mole), and cumyl chloride (0.14 mole) the theoretical yield was considered to be 1.0 mole of peroxide.

If the halide is ignored as a source of peroxide, then the yield figures given herein must be adjusted by the factor (mole of olefin/mole of olefin+mole of halide). Thus in a run where the reported yield for the above dicumyl peroxide preparation is 75%, the yield based on olefin charged is 87.1%. This is obtained as follows:

$$\frac{75}{0.86/1.0} = 87.1$$

UTILITY

The peroxides produced herein are useful for all purposes in which known peroxides of this type are used. Examples 13 and 14 demonstrate the polyethylene cross-linking ability of a number of peroxides produced by the process of the invention.

EXAMPLE 1. Dicumyl Peroxide

Into a 100 ml. open-top, jacketed reactor was placed 19.2 g. (0.162 m.) of α-methylstyrene, 4.4 g. (0.0285 m.) of distilled cumyl chloride and 37 g. (0.20 m.) of 82% assay cumene hydroperoxide. The mixture was stirred at 40°±2° C. for 5 hours. The reaction mixture was cooled to 20° and then stirred for 15 minutes with 40 ml. of 20% sodium hydroxide solution. The aqueous layer was discarded. The washing with caustic was repeated twice and the organic layer washed with 50 ml. portions of 20% sodium chloride solution until neutral. The organic layer was added to 400 ml. of water and the mixture distilled at 80–90 mm. on a steam bath until no further oil came over with the water. The pot residue was stirred vigorously and cooled to 0° by adding ice.

The colorless dicumyl peroxide which crystallized was collected in a Buchner funnel by filtration, washed with water and then air-dried. The solid dicumyl peroxide weighing 35.4 g. assayed 90.8% (corrected yield 59.5%) and contained less than 0.5% cumeme hydroperoxide.

EXAMPLE 2. Dicumyl Peroxide

A mixture of 182 g. (1.0 m.) of 83.5% cumene hydroperoxide, 101.5 g. (0.86 m.) of α-methylstyrene and 23.8 g. (0.14 m.) of cumyl chloride was stirred at 40°±1° C. for 5 hours (external heat required). The mixture was cooled to room temperature and washed with three 50 ml. portions of 20% sodium hydroxide solution (washing period 5 minutes first wash and 10 minutes second and third wash). The organic layer was washed with five 300 ml. portions of 25% sodium chloride solution.

The wet crude product, weighing 270 g. was mixed with 1 liter of water. The mixture was distilled at 80–90 mm. until no further oil came over into the distillate. The pot residue consisting of dicumyl peroxide and water was stirred vigorously while 200 g. of ice was added. Dicumyl peroxide crystallized in colorless shiny needles. Yield 173 g.; assay 95% (corrected yield 60.0%); hydroperoxide content 1.3%.

The oily material from the distillate weighed 48.5 g. and consisted of 26% cumene, 56% α-methylstyrene and lesser amounts of acetophenone and cumyl alcohol. This recovered material was used without purification in a subsequent run from which a 55.1% yield of dicumyl peroxide was obtained.

EXAMPLE 3. Dicumyl Peroxide

A. A mixture of 37 g. (0.20 m.) of 82% cumene hydroperoxide, 5.45 g. (0.027 m.) of cumyl bromide and 20.4 g. (0.173 m.) of α-methylstyrene was stirred for 5 hours at 40° C. The product work-up was the same as that described in Example 1. The yield of dicumyl peroxide was 41 g., assay 90.8% (corrected yield 68%).

B. Under identical conditions but using cumyl chloride instead of cumyl bromide, the yield was 55.8%.

EXAMPLE 4

1,4 Bis[α-(t-butylperoxy)isopropyl]benzene

Recrystallized p-diisopropenylbenzene (13.4 g., 0.086 m.) and 3.2 g. (0.014 m.) of 1,4 bis(α-chloroisopropyl) benzene were dissolved in 50 ml. of benzene. To the benzene solution was added 25.25 g. (0.25 m.) of 85% t-butyl hydroperoxide [1.45 m of —OOH per mole of isopropenyl] and the resulting mixture stirred for 2.5 hours at 30° C. The reaction mixture was washed with four 50 ml. portions of 10% potassium hydroxide solution, three 50 ml. portions of water and then dried over magnesium sulfate. The filtered solution was stripped in vacuo. The product, an off-white solid, weighed 29.8 g. (85.6% yield) and melted from 69°–74° C. Recrystallization from isopropyl alcohol (4 ml. per g. of product) afforded pure white crystalline 1,4 bis[α-(t-butylperoxy)isopropyl] benzene melting at 76°–77° C. (Reported m.p. 77°).

At longer reaction times, the yield decreased; 81% (5 hrs. at 30°); 78% (7.5 hrs. at 30°).

When the molar ratios of —OOH to isopropenyl was raised from 1.45 to 1.76, the yield increased to 91% of theory.

EXAMPLE 5

A. 4-(α-Chloroisopropyl)α,α,α′,α′-tetramethylphthalan

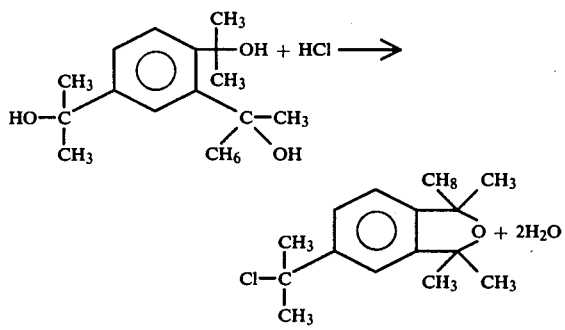

Into a 250 ml., jacketed reactor was placed 25.2 g. (0.1 m) of 1,2,4 tris(α-hydroxyisopropyl)benzene, 60.8 g. of concentrated hydrochloric acid and 150 ml. of heptane. The mixture was stirred for 7½ hours at 25° C. The aqueous layer was drawn off and discarded. The heptane layer was dried over magnesium sulfate, filtered and concentrated in vacuo. The residue, gummy solid, weighing 26 g., was dissolved in a small amount of pentane and cooled to −20° C. A colorless crystalline product was filtered off and air-dried, yield 14.5 g.; m.p. 77°–80°, chlorine (theory) 13.9%, (found) 13.7%. The infra-red spectrum has a moderate C—Cl absorption at 760 cm.$^{-2}$, a strong absorption at 890 cm$^{-2}$ attributable to the

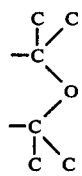

structure, a strong C—O absorption at 1100 cm$^{-2}$ and no H—O absorption.

B. Using the procedure of Example 1, t-Butylhydroperoxide, 4-isopropenyl-α,α,α′,α′-tetramethylphthalan, and chlorophthalan prepared in A above were reacted and the product 4-[α-(t-butylperoxy) isopropyl]-α,α,α′,α′ tetramethylphthalan recovered. This assayed 100% at a yield of 87% and had a m.p. of 81°–82° C.

EXAMPLE 6

Numerous other peroxides were made according to one or another of the earlier examples. These peroxides and the corrected yield are listed below.

| | Peroxide | Corr. Yld % |
|---|---|---|
| 1. | 1-(2-Naphthyl)-1-methylethyl t-butyl | 68. |
| 2. | 2-Phenyl-4-Methyl-2-pentyl t-butyl | 54. |
| 3. | 1,1-diphenylethyl t-butyl | 58. |
| 4. | p-t-Butylcumyl t-butyl | 57. |
| 5. | 1,3,5-Tris[α-(t-butylperoxy)isopropyl]benzene | 81.5 |
| 6. | 1-Phenylcyclohexyl t-butyl | 10. |
| 7. | 1-(4-biphenylyl)-1-methylethyl t-butyl | 20. |
| 8. | p-Methylcumyl cumyl | 78. |
| 9. | p-Isopropylcumyl cumyl | 98.5 |
| 10. | p-t-Butylcumyl cumyl | 85.8 |
| 11. | α-t-Butyl-α-methylbenzyl cumyl | 30. |
| 12. | t-Butyl p-methylcumyl | 55. |
| 13. | t-Butyl p-isopropylcumyl | 90. |
| 14. | p-Chlorocumyl cumyl | 64. |
| 15. | m-Chlorocumyl cumyl | 49. |
| 16. | p-Fluorocumyl cumyl | 76. |

EXAMPLE 7

Effect of Feed Proportions on Peroxide Yield

The effect of feed proportions charged to the reactor on the yield of dicumyl peroxide (DCP) is demonstrated by the following series of runs, each series was carried out according to the procedure of Example 1 at a fixed temperature-time relation, while the proportions of cumene hydroperoxide (CHP), α-methylstyrene (MeS), and cumyl chloride (CX) were varied from run to run. The results of these two series are set out below.

| Temp °C. | Time Hours | CHP mole | MeS mole | CX mole | DCP % Yield(1) |
|---|---|---|---|---|---|
| 40 | 2.5 | 1.0 | 1.72 | 0.28 | 52.3 |
| 40 | 2.5 | 1.0 | 1.22 | 0.28 | 56.4 |
| 40 | 2.5 | 1.0 | 0.82 | 0.28 | 58.5 |
| 40 | 2.5 | 1.0 | 0.72 | 0.28 | 59.4 |
| 40 | 2.5 | 1.5 | 0.72 | 0.28 | 64.7 |
| 30 | 5.0 | 1.0 | 0.86 | 0.14 | 57.6 |
| 30 | 5.0 | 1.25 | 0.86 | 0.14 | 71.7 |
| 30 | 5.0 | 1.67 | 0.86 | 0.14 | 85.0 |

(1)Maximum possible yield, corrected for assay, assumed to be 1.0 mole of DCP.

At a fixed temperature and time, the yield of peroxide is controlled by the amount of hydroperoxide present. The yield is benefited by having an excess of the hydroperoxide present in the feed and this is especially evident when operating at the lower temperatures.

EXAMPLE 8

Effect of Reaction Time on Peroxide Yield

The effect of reaction time on the yield of dicumyl peroxide (DCP) is demonstrated by a series of runs where in each series the temperature and proportion of cumene hydroperoxide (CHP), α-methylstyrene (MeS), and cumyl chloride (CX) was fixed. A number of series was carried out at 40° C. using different proportions in each series. Another series was carried out at 30° C. Each run in each series was carried out according to the procedure of Example 1. The results of these runs are set out below.

| Temp °C. | CHP mole | MeS mole | CX mole | DCP % Yield at Hours(1) | | | |
|---|---|---|---|---|---|---|---|
| | | | | 1. | 2.5 | 5. | 7.5 |
| 40 | 1.0 | 0.93 | 0.07 | — | 26.5 | — | — |
| 40 | 1.0 | 0.86 | 0.14 | 37.6 | 54.8 | 60.0 | 55.6 |
| 40 | 1.0 | 0.72 | 0.28 | — | 59.4 | 55.8 | — |
| 40 | 1.0 | 0.59 | 0.41 | 28.6 | 48.5 | — | — |
| 30 | 1.0 | 0.86 | 0.14 | — | 38.1 | 55.7 | 61.5(2) |

(1)Based on cumyl hydroperoxide, corrected for assay.
(2)At 10 hours, the yield of DCP was 60.8%.

At a given set of operating conditions, the yield of peroxide is increased with increasing time of reaction. However, at each set of conditions, prolonged time results in a decrease in yield—undoubtedly because of decomposition of the peroxide product, as the data show longer times are permissible at the lower temperature of reaction.

EXAMPLE 9

Effect of Reaction Temperature on Peroxide Yield

The effect of reaction temperature on the yield of dicumyl peroxide (DCP) is demonstrated by a series of runs where in each series the proportion of cumene hydroperoxide (CHP), α-methylstyrene (MeS), and cumyl chloride (CX) and the time of reaction were fixed. A number of series was carried out with each run in each series being carried out according to the procedure of Example 1. The results of these runs are set out below.

| Time Hours | CHP mole | MeS mole | CX mole | DCP % Yield at Temp. °C. (1) | | | |
|---|---|---|---|---|---|---|---|
| | | | | 30 | 40 | 50 | 60 |
| 2.5 | 1.0 | 0.86 | 0.14 | 38.1 | 54.8 | 58.2 | 48.3 |
| 2.5 | 1.0 | 0.72 | 0.28 | 52.6 | 59.4 | 55.3 | — |
| 5.0 | 1.0 | 0.86 | 0.14 | 55.7 | 59.5 | 45.0 | — |

(1) Maximum possible yield of peroxide, corrected for assay, assumed to be 1.0 mole of DCP.

At a given set of operating conditions, the yield of peroxide is increased with increasing temperature but only to a particular optimum temperature. Thereafter, the yield decreases with increasing temperature—undoubtedly because of the decomposition of the peroxide product. It is evident from Examples 8 and 9 that there is an optimum time-temperature relation at each proportion of the feed charged to the reactor which produces a maximum yield of peroxide product. In general, the best yields are obtained, at a given feed proportion, by associating the higher temperatures with the shorter times. However, these examples show that it is a reasonably simple matter to determine the optimum conditions for a given feed.

Test 10. Dicumyl Peroxide by direct reaction of hydroperoxide and cumyl chloride.

A 100 ml. round-bottom flask was equipped with thermometer, mechanical stirrer, addition funnel and vacuum take-off. To the flask was charged 27.8 g. (0.15 m.) of 82% cumene hydroperoxide. The vacuum take-off was connected to a manometer and a water pump; the pressure in the flask was reduced to 0.02 atmosphere. The purpose of operating under reduced pressure was to remove hydrogen chloride as soon as it was formed in the reaction.

To the addition funnel was charged 23.2 g. (0.15 m.) of cumyl chloride. The reaction flask was surrounded by a water bath. Dropwise addition of cumyl chloride was begun. The reaction was very exothermic and a long addition time (3 hours) was required. The reaction mixture in the flask became black. After being stirred for an additional 1.5 hours under reduced pressure, the reaction mixture (with a strong phenolic odor) was transferred to a separatory funnel; it was washed with 200 ml. of 20% sodium hydroxide solution then with 100 ml. portions of water until neutral. The dried (magnesium sulfate) product mixture was filtered and stripped in vacuo. The residue (9.4 g.) was very dark and contained only 0.17% active oxygen. The active oxygen content of dicumyl peroxide is 5.94%. It is probable that no dicumyl peroxide was formed in this procedure.

EXAMPLE 11

Dicumyl Peroxide—Purification Procedures

A. High temperature vacuum stripping

A mixture of 36.4 g. (0.2 m.) of 83.5% cumene hydroperoxide, 5 g. (0.0325 m.) of cumyl chloride and 22.4 g. (0.19 m.) of α-methylstyrene was stirred for 2½ hours at 40° C. The reaction mixture was washed with 50 ml. of water, four 50 ml. portions of 10% potassium hydroxide solution, 50 ml. of water and finally saturated sodium chloride solution. The organic layer was dried over sodium sulfate and filtered. The filtrate was then heated gradually to 85°–90° C. at 1 mm. pressure. The product was distilled under 1 mm. of pressure for 90 minutes at 85°–90° C. The amber residue, weighing 36.1 g., was allowed to cool to room temperature; it spontaneously crystallized on standing overnight. The product assayed 85.5% (corrected yield 57.2%) and contained 5.9% hydroperoxide. The product was decolorized by treatment with charcoal in methanol and recrystallization from methanol.

The average assay for 13 dicumyl peroxide preparations using high temperature vacuum stripping was 79.0±8.1% and average hydroperoxide content was 4.1±0.3%.

B. Liquid Water Vaporization

Another run was carried out under conditions identical to those described in A above except that after washing with saturated sodium chloride, the wet crude product was mixed with 300 ml. of water and distilled at 100 mm. pressure until no further oil came over in the distillate. The pot residue was cooled by dumping in 50 g. of ice; the dicumyl peroxide spontaneously crystallized as colorless needles. The dicumyl peroxide was filtered off under vacuum, washed with water and then allowed to air dry. The colorless crystalline product weighed 34 g. and assayed 94.3% (corrected yield 59.4%) and contained 0.5% hydroperoxide. No further purification was necessary.

The average assay for 23 dicumyl peroxide preparations using the liquid water vaporation procedure was 95.6±2.0% and average hydroperoxide content was 1.45±0.8%.

EXAMPLE 12 t-Butyl Cumyl Peroxide—Comparison of Cumyl chloride and sulfuric acid preparation and purification procedure A. Sulfuric Acid Route Into a jacketed reactor was charged 48.3 g (0.5 m.) of 93.2% t-butyl hydroperoxide. The reaction temperature was maintained at 0° C. by circulating cold brine through the reactor jacket, while 50 g. of 70% sulfuric acid was slowly added to the hydroperoxide. Then 70.8 g. (0.6 m.) of α-methylstyrene was added dropwise over a 30 minute period after which the reaction product mixture was stirred for 3 hours at 0°. The reaction product mixture was then washed with 100 ml. of water, 100 ml. of 10% potassium hydroxide solution and finally with 100 ml. portions of water until neutral. The organic layer was separated, dried (magnesium sulfate), filtered and stripped in vacuo at 1–3 mm. at ambient temperature for 2 hours. The residue (73.0 g.) assayed 72.1% t-butyl cumyl peroxide by vapor phase chromatography. The yield was 50.7%.

The crude product was distilled at 0.05 mm. through a Vigreux column; the cut boiling at 47°–50° was redistilled and a heart cut taken at 45°–47°. This heart cut assayed 92.7%; it darkened on standing.

A series of ten runs were carried out under varying conditions of time, temperature and concentration of acid. The yield ranged from 5.5% to 50.7% and assays from 13.2% to 73.2%.

B. Cumyl Chloride Route

A mixture of 126 g. (1.2 m.) of 85.8% t-butyl hydroperoxide, 101.5 g. (0.86 m.) of α-methylstyrene and 21.6 g. (0.14 m.) of cumyl chloride was stirred for 5 hours at 30°±2° C. The reaction mixture was washed (15 minutes) with two 50 ml. portions of 10% potassium hydroxide, then with six 50 ml. portions of saturated sodium chloride solution. The organic layer (197.3 g.) contained 79.8% of t-butyl cumyl peroxide. The yield was 75.7%.

The crude peroxide was purified by the liquid water vaporization procedure of Example 11. The purified peroxide assayed 89.9%; it remained colorless in storage at room temperature.

EXAMPLE 13

Crosslinking of Polyethylene

The peroxide (usually 0.01 equivalents of active oxygen per 100 g. of polyethylene) was dry blended with finely divided polyethylene "Microthene" TM on a ball mill. The peroxide-containing polyethylene was then moulded into 5"×5"×0.07 plaques which were then cured in a platen press at a ram pressure of 20,000 psi. for 30 minutes at the temperatures specified. The "percent crosslinked" was determined by extracting the uncrosslinked portion with xylene at 80° C. The curing results are set out below.

| Peroxide | % Crosslinked at Cure Temp. (°F.) | | |
|---|---|---|---|
| | 320° | 340° | 375° |
| t-Butyl cumyl peroxide | 94.0 | 95.1 | 95.2 |
| t-Butyl p-methylcumyl peroxide | 88.6 | 90.3 | 89.5 |
| t-Butyl p-isopropylcumyl peroxide | 84.6 | 85.8 | 83.5 |
| t-Butyl p-t-butylcumyl peroxide | 92.6 | 94.0 | 93.7 |

EXAMPLE 14

Crosslinking of Polyethylene

The peroxide (usually 0.01 equivalents of active oxygen per 100 g. of polyethylene) was milled into DYNH-1 TM, a grade of low-density polyethylene on a two-roll mill. The milled sheet was cut into plaques and cured in a platen press at a ram pressure of 20,000 psi for 30 minutes at the temperature below. The "Percent crosslinked" was determined by extracting the uncrosslinked portion with xylene at 80° C. The results are set out below.

| Peroxide | % Crosslinked at Cure Temp. (°F.) | | |
|---|---|---|---|
| | 320° | 340° | 375° |
| Dicumyl peroxide | 89.5 | 89.8 | 89.7 |
| p-Methylcumyl cumyl peroxide | 83.6 | 83.1 | 83.0 |
| p-Isopropylcumyl cumyl peroxide | 83.0 | 83.2 | 82.9 |
| p-t-Butylcumyl cumyl peroxide | 87.7 | 87.8 | 87.2 |
| p-chlorocumyl cumyl peroxide | 85.9 | 85.6 | 85.0 |
| 1,4-bis[α-(t-butylperoxy)isopropyl]benzene | 89.1 | 91.9 | 91.3 |
| 1,3,5-tris[α-(t-butylperoxy)isopropyl]benzene | 89.5 | 91.6 | 91.2 |
| 4-[α-(t-Butylperoxy)isopropyl] α,α,α',α'-tetramethylphthalan | 87.1 | 89.3 | 89.1 |
| 2,5-Bis(cumylperoxy)-2,5-dimethylhexane | 85.0 | 85.2 | 84.2 |
| 2,5-Bis(cumylperoxy)-2,5-dimethylhexyne-3 | 81.0 | 86.9 | 88.1 |
| 2-[α-(t-butylperoxy)isopropyl]-naphthalene | 87.6 | 89.2 | 89.2 |
| 2-[α-(t-butylperoxy)isopropyl] naphthalene | 79.8 | 79.4 | 78.8 |
| 1,3-Bis[α-(t-butylperoxy)isopropyl]benzene | 89.3 | 91.7 | 91.4 |
| 2-Fluorocumyl cumyl peroxide | 89.1 | 89.6 | 88.8 |

Thus, having described the invention, what is claimed is:

1. A process for purifying, an impure organic peroxide having the general formula

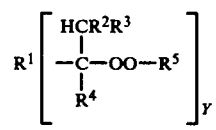

produced by a solvolysis reaction of an aralkyl halide with a hydroperoxide in the presence of an olefin corresponding to the dehydrohalogenated aralkyl halide wherein the impurities are generally substituted benzene derivatives, said impure peroxide being essentially free of acidic materials and said impurities having an appreciable lower boiling point than said peroxide which process comprises charging said impure peroxide along with about 2–10 parts by weight of liquid water, based on said impure peroxide, to a distillation zone and vaporizing water and impurities at a temperature of about 30°–80° C. at a pressure of about 0.01–0.5 atmospheres and continuing said vaporization until essentially no oily liquid is obtained in a condensor receiving vapors from said zone, under conditions such that a substantial amount of liquid water is present in said zone in contact with peroxide product, wherein (a) Y is an integer equal to 1, 2 or 3;
(b) $R^1$ is phenyl or naphthyl;
(c) $R^2$ and $R^3$ are each H, alkyl, cycloalkyl, phenyl or a corresponding halo-substituted radical;
(d) $R^4$ is alkyl, cycloalkyl, phenyl or a corresponding halo-substituted radical;
(e) $R^2$ and $R^3$ may join with the common carbon to which they are attached to form the cyclic group;
(f)

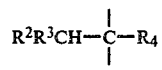

may be a cyclic group;
(g)

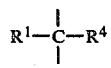

may be a fused ring group; and
(h) $R^5$ is an aliphatic or cycloaliphatic hydrocarbon radical.

2. The process of claim 1 wherein said impure peroxide charge is the product mixture produced from the process which consists essentially of:

(1) reacting an olefin, a reactive organic halide and an organic hydroperoxide, under substantially anhydrous conditions, at a temperature in the range of about 0°–60° C., where
(2) said olefin has the formula:

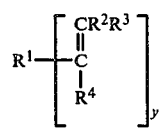

where
(a) Y is an integer equal to 1, 2 or 3;
(b) $R^1$ is a phenyl or naphthalene group;
(c) $R^2$ and $R^3$ are each H, alkyl, cycloalkyl, phenyl, or a corresponding halo substituted radical, or $R^2$ and $R^3$ join with the common carbon atom to which they are attached or with

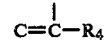

to form a cyclic group;
(d) $R^4$ is alkyl, cycloalkyl, phenyl, or a corresponding halo substituted radical; and
(e) when $R^1$ is substituted on more than one ring carbon atom, not more than one ring carbon atom ortho to a

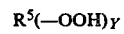

group can be joined to a substituent group;
(3) said reactive organic halide has the formula:

where X is Br or Cl;
(4) said organic hydroperoxide has the formula:

$$R^5(-OOH)_Y$$

where $R^5$ is an aliphatic or cycloaliphatic hydrocarbon radical, or a corresponding halo substituted radical;
(5) the mole ratio of hydroperoxide groups in said organic hydroperoxide charged to the ethylenic bonds in said olefin charged is 2–1.1 to 1; and
(6) said halide is charged in an amount of about 2–20 mole percent based on olefin charged;
said product mixture having been treated with aqueous alkali metal hydroxide to remove organic halide and unreacted hydroperoxide.

3. The process of claim 2 wherein said impure peroxide charge was prepared in a reaction time of about 1 to 12 hours, the longer times being associated with the lower temperatures and the halide is charged in an amount of about 10 to 20 mole percent based on olefin charged.

4. The process of claim 1 wherein said impure peroxide is the dicumyl peroxide product mixture obtained by the process which consists essentially of reacting at about 30° C. for about 5 hours cumene hydroperoxide, alpha-methylstyrene and cumyl chloride, which compounds has been charged to the reaction zone in a mole ratio of 1.25; 0.86: 0.14 and treating the reaction product mixture with aqueous alkali metal hydroxide to remove cumyl chloride and cumyl hydroperoxide to obtain a product mixture including dicumyl peroxide.

* * * * *